(12) United States Patent
Kurumatani et al.

(10) Patent No.: US 6,653,345 B2
(45) Date of Patent: Nov. 25, 2003

(54) C-C CHEMOKINE SYNTHESIS INHIBITOR

(75) Inventors: Hajimu Kurumatani, Kanagawa (JP); Rie Sasaki, Kanagawa (JP); Hiroki Kumagai, Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 10/139,658

(22) Filed: May 6, 2002

(65) Prior Publication Data

US 2002/0193427 A1 Dec. 19, 2002

Related U.S. Application Data

(63) Continuation of application No. 09/508,576, filed as application No. PCT/JP98/04164 on Sep. 16, 1998, now abandoned.

(30) Foreign Application Priority Data

Sep. 16, 1997 (JP) .............................................. 9-250966

(51) Int. Cl.$^7$ ...................... A61K 31/343; C07D 307/77
(52) U.S. Cl. ........................................ 514/468; 549/458
(58) Field of Search ........................... 514/468; 549/458

(56) References Cited

U.S. PATENT DOCUMENTS

| | | | |
|---|---|---|---|
| 4,474,802 A | 10/1984 | Ohno et al. | |
| 5,496,850 A | 3/1996 | Mutoh et al. | |
| 5,506,265 A | 4/1996 | Blitstein-Willinger | |

FOREIGN PATENT DOCUMENTS

| | | |
|---|---|---|
| JP | 7-188205 | 7/1995 |

OTHER PUBLICATIONS

Tanaka H., et al., "The effect of a synthetic 7-tiaprostaglandin $E_1$ derivative, TEI-6122, on monocyte chemoattractant protein-1 induced chemotaxis in THP-1 cells", British Journal of Pharmacolgy, 1995, vol. 116, No. 14, pp. 2298–2302.

P. Conti et al., Augmentation of monocyte chemotactic protein-1 and mRNA transcript in chronic inflammatory states induced by potassium Permanganate (KmnOr) in vivo, 1997, Immunology92, pp. 300–306.

Ali Akoum et al., "Increased monocyte chemotactic protein-1 level and activity in the peripheral blood of women with endometriosis", 1996, Am. J. Obstet Gumecol, 175, pp. 1620–1625.

Theodore J. Stadiford et al., "Expression and regulation of chemokines in bacterial pneumonia", 1996, Journal of Leukocyte Biology, vol. 59, pp. 24–28.

Raffaele Badolato et al., Leishmania major: Infection of Human Monocytes Induces Expression of IL–8 and MCAF[1,2]", 1996, Experimental Parasitology, 82, pp. 21–26.

Luca Mazzucchelli et al., Differential in situ Expression of the Genes Encoding the Chemokines MCP–1 and Rantes in Human Inflammatory Bowel Disease, 1996, Journal of Pathology. vol. 178: pp. 201–206.

Richard B. Goodman et al., "Inflammatory Cytokines in Patients with Persistence of the Acute Respiratory Distress Syndrome", 1996, Am. J. Respir. Crit. Care Med., vol. 154, pp. 602–611.

Y. Okuda et al., Acute Effect of Beraprost Sodium on Lower Limb Circulation in Patients with Non–Insulin–Dependent Diabetes Mellitus–Evaluation by Color Doppler Ultrasonography and Laser Cutaneous Blood Flowmetry, 1996, Prostaglandis, vol. 52, pp. 375–384.

Nigishi Hotta et al., Effects of Beraprost Sodium and Insulin on the Electroretinogram, Nerve Conduction, and Nerve Blood Flow in Rats with Streptozotocin–Induced Diabetes, 1996, Diabetes, vol. 45, pp. 361–366.

Hidekazu Yamada et al., Rantes mRNA Expression in Skin and Colon of Patients with Atopic Dermatitis, 1996, Int. Arch. Allergy Immunol., vol. 111, (suppl.1), pp. 19–21.

Y. Utsunomiya et al., Attenuation of immune complex nephritis in NZW/WF$_1$ mice by a prostacyclin analogue, 1995, Clin. Exp. Immunol., vol. 99, pp. 454–460.

Fumio Umeda et al., "Prostaglandins and Diabetic Nephropathy", 1995, Journal of Diabetes and its Complications, vol. 9, pp. 334–336.

Bruce D. Car et al., Elevated IL–8 and MCP–1 in the Bronchoalveolar Lavage Fluid of Patients with Idiopathic Pulmonary Fibrosis and Pulmonary Sarcoidosis, 1994, Am. J. Respir. Crit. Car Med., vol. 149, pp. 655–659.

Yuji Ueno et al., "Beraprost Sodium Protects Occlusion/Reperfusion Injury in the Dog by Inhibition of Neutrophil Migration", 1994, Gen. Pharmac., vol. 25, No. 3, pp. 427–432.

Alisa E. Koch et al., "Enhanced Production of Monocyte Chemoattractant Protein–1 in Rheumatoid Arthritis", 1992, The Journal of Clinical Investigation, Inc., vol. 90, pp. 772–779.

Primary Examiner—Charanjit S. Aulakh
(74) Attorney, Agent, or Firm—Piper Rudnick LLP (57) ABSTRACT

A method of inhibiting mammalian C—C chemokine production by using a mammalian C—C chemokine synthesis inhibitor containing a prostaglandin I derivative as an active component to treat a variety of circulatory diseases, inflammation, allergic diseases, and renal diseases.

9 Claims, 8 Drawing Sheets

Fig. 1 p<0.01 vs BPS 0

C-C CHEMOKINE SYNTHESIS INHIBITOR

This application is a continuation of application Ser. No. 09/508,576, filed Apr. 19, 2000, now abandoned, which is a 371 PCT/J98/04164, filed Sep. 16, 1998.

TECHNICAL FIELD

The present invention relates to a mammalian C—C chemokine production inhibitor comprising a prostanoic acid derivative as an active component.

BACKGROUND ART

In 1987, Matsushima et al. isolated IL-8 as a neutrophilic chemotactic factor from a culture supernatant of human peripheral blood monocytes stimulated by a popolysaccharide LPS, and then purified and cloned molecules having a migrating activity for many leukocytes. These molecules have a common structure, and are thus generically named "chemokine". Chemokine mainly has high affinity for heparin, and the common property that it is synthesized as a precursor composed of about 100 amino acids, and then secreted in a mature type comprising about 70 amino acids.

Chemokine generally has four cysteine residues, and is roughly classified into C—X—C chemokine comprising an amino acid held between the first two cysteine residues, and C—C chemokine having no amino acid between the cysteine residues. C—X—C chemokine is also called α chemokine, and C—C chemokine is called β chemokine. The C—C chemokine family is a generic name of a group of low-molecular-weight proteins having about 30% of homology at the amino acid level, and cysteine at the same four positions.

Monocyte chemoattractant protein-1 (MCP-1) also named a monocyte chemotactive activating factor (MCCAF) or a glioma-derived monocyte chemotactic factor(GDCF), and is a C—C chemokine protein comprising 76 amino acids and four cysteine residues. The identification and gene cloning of MCAF, MCP-1 or GDCF have been reported (K. Matsushima et al., J. Exp. Med., 169, 1485–1490, 1989, Y. Furutani et al., Biochem. Biophys. Res. Commun., 159, 249–255, 1989, E. R. Robinson et al., Proc. Natl. Acad. Sci. USA, 86, 1850–1854, 1989, T. Yoshimura et al., FEBS Letters, 244, 487–493, 1989) These documents also disclose methods of producing MCP-1. In the present invention, MCP-1 is an abbreviated name and includes GDCF and MCAF hereinafter.

MCP-1 is produced from hemocytic cells such as monocytes, macrophages, and lymphocytes, as well as various cells such as fibroblasts, endothelial cells, smooth muscle cells, various tumor cells, and the like by stimulation with IL-1, TNF, IFNγ-, LPS, phorbol ester (TPA), or the like, and MCP-1 is known to cause accumulation of very strong monocytes and/or macrophages in a pathogenic region. MCP-1 also has a chemotactic action and activating action on basophils and T cells.

Other known proteins belonging to the C—C chemokine family include RANTES, LD78, ACT2, I-309, MCP-2, MCP-3, JE, MIP-1α, MIP-1β, TCA-3, eotaxin, and the like. Of these proteins, MCP-2, MCP-3 (K. B. M. Reid, Immunol. Today 10, 177–180, 1989), RANTES (P. N. Barlow et al., J. Mol. Biol. 232, 268–284, 1993), and JE (B. J. Rollins et al., Proc. Natl. Acad. Sci. USA, 85, 3738–3742, 1988) are known to induce chemotaxis of monocytes and/or macrophages to a pathogenic region. RANTES also exhibits the strong chemotactic ability for basophils, eosinophils, and T-cells, and is related to chronic rheumatoid arthritis, endarterial hyperplasia after organ transplantation, rejection after organ transplantation, and allergic diseases. MIP-1α is known to exhibit the chemotactic action on basophils, eosinophils, T-cells, B-cells, and NK-cells, and eotaxin has strong chemotactic action on eosinophils.

Pathological progress of migration of eosinophils and basophils is frequently observed in acute serious inflammation, chronic intractable inflammation, bronchial asthma, allergic diseases, parasitic diseases, tumors, eosinophilic gastroenteritis, peptic ulcer, valvular diseases, multiple sclerosis, osteoporosis, and organ re-perfusion disorder. Although migration of monocytes and macrophages to a pathogenic region is also observed in general inflammation, it is observed particularly in acute serious inflammation, chronic intractable inflammation, and allergic diseases, and also observed in nephritis, pneumonocirrhosis, arteriosclerosis, and malignant tumors.

It is known that diabetes highly frequently causes great vessel diseases such as arteriosclerosis, and microangiopathy causing complications such as diabetic neuropathy, diabetic nephropathy, diabetic retinopathy, and the like. However, it is thought to be important for the angiopathy that microphages are bonded to the endothelial cells and infiltrated into the vessel walls.

It is also known that in lung diseases, microphages are increased in the lung, and macrophages play an important role for fibrogenesis in the lung. Accumulation of macrophages is also observed in an affected part of chronic rheumatoid arthritis (RA).

Conventionally, a steroidal agent or non-steroidal anti-inflammatory agent is used for the above-described diseases. However, such medicines are known to suppress leukocyte migration, and at the same time, suppress the functions of many types of cells, thereby causing the problem of causing various serious side effects.

Prostaglandin (PG) includes a group of compounds naturally existing, exhibiting a variety of physiological activities, and having a common prostanoic acid skeleton. The natural PG compounds are classified into PGA, PGB, PGC, PGD, PGE, PGF, PGG, PGH, PGI, and PGJ by the structural characteristics of five-member rings, and further classified into sub-classes 1, 2, 3, etc. by the presence of unsaturation and oxidation. Also, many synthetic compounds analogous to these PG compounds are known. Of these PG compounds, a typical PGI derivative $PGI_2$ is referred to as "prostacyclin" (refer to Nature, Vol. 268, p688, 1976), and is known as a substance having strong platelet aggregation inhibiting action and peripheral vasodilating action. As compounds in which instability of the $PGI_2$ is significantly improved, Japanese Examined Patent publication Nos. 2-12226, 2-57548 and 1-53672 disclose $PGI_2$ derivatives having a skeleton in which the structure of an exoenol ether portion, which is a characteristic structure of $PGI_2$, is converted into an inter-m-phenylene type. Other known compounds in which stability of prostaglandin is improved include ataprost, iloprost, clinprost, ciprosteni, naxaprost, taprostene, cicaprost, pimilprost, CH-169, and CS570 (refer to Gendai-Iryosha, "Generals of Prostaglandin" No. 1, p. 123, 1994; New Drugs of Tomorrow, p. 15-IV-185, 1996; New Drugs of Tomorrow, p. 15-III-551, 1996). However, it is unknown that these prostanoic acid derivatives have the action to inhibit directly C—C chemokine production.

It is an object of the present invention to provide a preventive and curative medicine for diseases for which conventional medicines are ineffective and cause serious side effects, such diseases being characterized by abnormal accumulation or activation of leukocytes such as monocytes and/or macrophages, eosinophils, basophils, and the like.

DISCLOSURE OF INVENTION

The present invention provides a C—C chemokine production inhibitor comprising a prostanoic acid derivative as an active component.

BRIEF DESCRIPTION OF THE DRAWINGS

FIG. 7 shows the effect of BPS administration on macrophage infiltration into glomeruli in a glomerulonephritis model (FIG. 7a), and on changes in renal gene expression (FIG. 7b).

BEST MODE FOR CARRYING OUT THE INVENTION

As prostanoic acid derivatives of the present invention, derivatives of any type of PGA, PGB, PGC, PGD, PGE, PGF, PGG, PGH, PGI, and PGJ, which have the prostanoic acid skeleton, and derivatives of any of the sub-classes 1, 2, 3, etc., which are by the presence of unsaturation and oxidation, may be used. These derivatives include not only natural compounds but also synthetic analogues. Although the basic skeleton of prostanoic acid generally has 20 carbon atoms, the carbon number of prostanoic acid used in the present invention is not limited. PGI derivatives preferably used in the present invention include $PGI_1$ derivatives, $PGI_2$ derivatives, $PGI_3$ derivatives, and salts thereof, but $PGI_2$ derivatives or salts thereof are preferably used. More preferably, 4,8-inter-m-phenylene prostaglandin $I_2$ derivatives represented by the following formula (I) or pharmacologically acceptable salts thereof are used.

[wherein $R^1$ represents the following:
  (A) $COOR^2$ wherein $R^2$ is:
    1) hydrogen or a pharmacologically acceptable cation;
    2) straight chain alkyl having 1 to 12 carbon atoms, or branched alkyl having 3 to 14 carbon atoms;

3) —Z—$R^3$
     wherein Z is a valence bond or straight chain or branched alkylene represented by $C_tH_{2t}$, wherein t represents an integer of 1 to 6, and $R^3$ represents cycloalkyl having 3 to 12 carbon atoms or substituted cycloalkyl having 3 to 12 carbon atoms and 1 to 3 substituents $R^4$ each of which is hydrogen or alkyl having 1 to 5 carbon atoms;
  4) —$(CH_2CH_2O)_n$$CH3$
     wherein n is an integer of 1 to 5;
  5) —Z—$Ar^1$
     wherein Z is defined above, and $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein a substituent is at least one of chlorine, fluorine, iodine, trifluoromethyl, alkyl having 1 to 4 carbon atoms, nitro, cyano, methoxy, phenyl, phenoxy, p-acetoamidobenzamide, —CH=N—NH—C(=O) —$NH_2$, —NH—C(=O) —Ph, —NH—C(=O) —$CH_3$ and —NH—C(=O)—$NH_2$);
  6) —$C_tH_{2t}COOR^4$
     wherein $C_tH_{2t}$ and $R^4$ are defined above;
  7) —$C_tH_{2t}N(R^4)_2$
     wherein $C_tH_{2t}N$ and $R^4$ are defined above;
  8) —$CH(R^5)$—$C(=O)$—$R^6$
     wherein $R^5$ is hydrogen or benzoyl, and $R^6$ is phenyl, p-bromophenyl, p-chlorophenyl, p-biphenyl, p-nitrophenyl, p-benzamidophenyl, or 2-naphthyl;
  9) —$C_pH_{2p}$—W—$R^7$
     wherein W is —CH=CH—, —CH=CR or —C≡C—, and $R^7$ is hydrogen or straight chain or branched alkyl or aralkyl having 1 to 30 carbon atoms, and p is an integer of 1 to 5; or
  10) —$CH(CH_2OR^8)_2$
     wherein $R^8$ is alkyl or acyl having 1 to 30 carbon atoms;
(B) —$CH_2OH$;
(C) —$C(=O)N(R^9)_2$
   wherein $R^9$ is hydrogen, straight chain alkyl having 1 to 12 carbon atoms, branched alkyl having 3 to 12 carbon atoms, cycloalkyl having 3 to 12 carbon atoms, cycloalkylalkylene having 4 to 13 carbon atoms, phenyl, substituted phenyl (wherein the substituent is defined in (A) (5)), aralkyl having 7 to 12 carbon atoms, or —$SO_2R^{10}$ wherein $R^{10}$ is alkyl having 1 to 10 carbon atoms, cycloalkyl having 3 to 12 carbon atoms, phenyl, substituted phenyl (the substituent is defined as the same as in (A) (5)), or aralkyl having 7 to 12 carbon atoms, two $R^9$ groups may be the same or different, and when one of the $R^9$ groups is —$SO_2R^{10}$, the other $R^9$ is not —$SO_2R^{10}$; or
(D) —$CH^2OTHP$ (THP is a tetrahydropyranyl group);
A is the following:
  1) $(CH_2)_m$—;
  2) —CH=CH—$CH_2$—;
  3) —CH2—CH=CH—;
  4) $CH_2$—O—$CH_2$—;
  5) —CH=CH—;
  6) —O—$CH_2$—; or
  7) —C≡C—;
  wherein m represents an integer of 1 to 3;
D is hydrogen, alkyl having 1 to 4 carbon atoms, chlorine, bromine, fluorine, formyl, methoxy or nitro;
G is —X—$C(R^{11})$ $(R^{12})OR^{13}$
  wherein $R^{11}$ is hydrogen, alkyl having 1 to 4 carbon atoms; $R^{13}$ is hydrogen, acyl having 1 to 14 carbon atoms, aroyl having 6 to 15 carbon atoms, tetrahydropyranyl, tetrahydrofuranyl, 1-ethoxythienyl, or t-butyl; X is the following:
1) —$CH_2$—$CH_2$—;
2) —CH=CH—; or
3) —C≡C—; and $R^{12}$ is the following:
1) straight chain alkyl having 1 to 12 carbon atoms, or branched alkyl having 3 to 14 carbon atoms;
2) —Z—$Ar^2$
   wherein Z is defined above, and $Ar^2$ represents phenyl, α-naphthyl, β-naphthyl, or phenyl substituted by at least one chlorine, bromine, fluorine, iodine, trifluoromethyl, alkyl having 1 to 4 carbon atoms, nitro, cyano, methoxy, phenyl or phenoxy;
3) —$C_tH_{2t}$$OR^{14}$
   wherein $C_tH_{2t}$ is defined above, and $R^{14}$ represents straight chain alkyl having 1 to 6 carbon atoms, branched alkyl having 3 to 6 carbon atoms, phenyl, phenyl substituted by at last one chlorine, bromine, fluorine, iodine, trifluoromethyl, alkyl having 1 to 4 carbon atoms, nitro, cyano, phenyl or phenoxy, cyclopentyl, cyclohexyl, or cyclopentyl or cyclohexyl substituted by 1 to 4 straight chain alkyl groups having 1 to 4 carbon atoms;
4) —Z—$R^3$
   wherein Z and $R^3$ are defined above;
5) —$C_tH_{2t}$—CH=C ($R^{15}$) $R^{16}$
   wherein $C_tH_{2t}$ is defined above, and $R^{15}$ and $R^{16}$ each represent hydrogen, methyl, ethyl, propyl, or butyl; or
6) —$C_uH_{2u}$—C≡C—$R^{17}$
   wherein u is an integer of 1 to 7, $C_uH_{2u}$ represents straight chain or branched alkyl, and $R^{17}$ represents straight chain alkyl having 1 to 6 carbon atoms;

E is hydrogen or —$OR^{18}$
   wherein $R^{18}$ represents acyl having 1 to 12 carbon atoms, aroyl having 7 to 15 carbon atoms, or $R^2$ (wherein $R^2$ is defined as the same as the above); and
the formula represents a d, l or dl form].

As described above, the prostanoic acid derivatives of the present invention inhibit the production of C—C chemokines, promotors of migration of leukocytes, thus inhibiting chemotaxis to a pathological region.

A typical example of a C—C chemokine of the present invention is MCP-1. It has been reported that MCP-1 is produced from hemocytic cells such as monocytes, macrophages, and lymphocytes, as well as various cells such as fibroblasts, endothelial cells, smooth muscle cells, various tumor cells, and the like by stimulation with IL-1, TNF, IFN-γ, LPS, phorbol ester (TPA), or the like. Although other examples of C—C chemokines include RANTES, LD78, ACT2, I-309, MCP-2, MCP-3, JE, MIP-1α, MIP-1β, TCA-3, eotaxin, and the like, C—C chemokine compounds are not limited to these compounds.

As a result of detailed study of the actions of prostanoic acid derivatives, the inventors found that the compounds have the ability to inhibit C—C chemokine production, leading to the achievement of the present invention. In the present invention, curable diseases are not limited as long as the diseases are related to abnormal accumulation of leukocytes, particularly monocytes and/or macrophages, eosinophils, basophils, and lymphocytes, accompanied with abnormal production of C—C chemokines.

Examples of such diseases include circulatory disorders, inflammation, allergic diseases, and renal diseases. More specifically, examples of the diseases include acute serious inflammation, chronic intractable inflammation, nephritis, glomerulonephritis, pyelitis, diabetic nephropathy, pneumonocirrhosis, pneumonia, ARDS, fibroma, ulcerative colitis, chronic rheumatoid arthritis, systemic lupus erythematodes, gout, bronchial asthma, atopic dermatitis, Crohn's disease, osteoarthritis, parasitic disease, eosinophilic gastroentritis, arteriosclerosis, arterial reocclusion after coronary arterial operation including PTCA, myocardial infarction, malignant carcinoma cutaneum metastasis, malignant sarcoma metastasis, diabetic microangiopathy, diabetic neuropathy, diabetic retinopathy, diabetic large artery disorder, osteoarthritis and malignant tumors, endarterial hyperplasia after organ transpiantation, rejection after organ transplantation, osteoporosis, peptic ulcer, organ re-perfusion disorders, valvulitis, multiple sclerosis, and endometriosis.

Any one of the prostanoic acid derivatives of the present invention is administered 1 to 3 times a day in a dose of 0.001 to 1000 mg/adult. Although the C—C chemokine production inhibitor of the present invention may contain at least one prostanoic acid derivative, the inhibitor can also be orally administered in the form of a solid containing the additives below.

Examples of such additives include an excipient such as starch, lactose, sucrose, glucose, mannitol, potassium carbonate, calcium sulfate, or the like; a binder such as starch, dextrin, gum arabic, tragacanth, methyl cellulose, gelatin, polyvinyl pyrrolidone, polyvinyl alcohol, or the like; a disintegrator such as starch, polyvinyl pyrrolidone, crystalline cellulose, or the like; a lubricant such as magnesium stearate, talc, or the like; a colorant; a flavor; and the like.

The prostanoic acid derivatives of the present invention can be used in various forms. Examples of the forms include conventional forms such as a tablet, a sugar-coated tablet, a powder, granules, a troche, a capsule, a pill, a syrup, a spray, and the like. The derivatives may also be parenterally administered in the form of a sterilized solution, and another solute such as sodium chloride, glucose, or the like can also be used in an amount sufficient for making the solution isotonic. The C—C chemokine production inhibitor of the present invention can be applied to the above-described oral administration as well as parenteral administration of injections, suppositories, etc.

EXAMPLES

The present invention will be described in detail below with reference to examples.

Example 1

Action on Amount of MCP-1 Production of Human Monocyte/Macrophage System Cells THP-1

Figure 1:
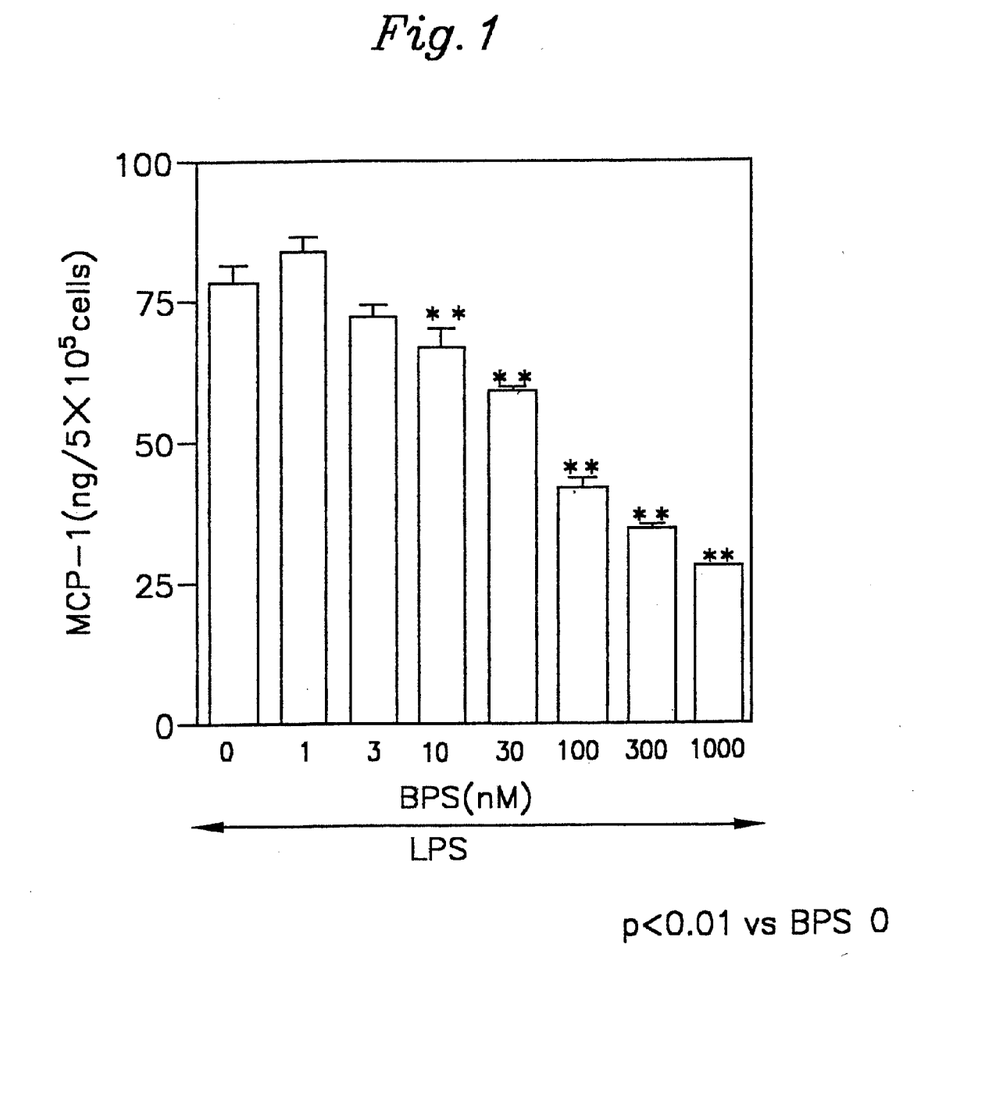
FIG. 1 shows the BPS action on MCP-1 production of THP-1 cells stimulated with LPS.

The action of beraprost (BPS) on MCP-1 production was examined by using human monocyte/macrophage system leukemic cells THP-1. Lipopolysaccharide (LPS: Difco Corp.) reactive substrains were isolated from THP-1 cells (obtained from ATCC Corp.), and cultured in a RPMI 1640 medium (Gibco Corp.) containing 10% FCS in a flask. The THP-1 cells ($1 \times 10^5$ cells) were dispensed to a 12-well plate, and activated with 10 μg/ml of LPS. BPS was added 5 minutes before LPS stimulation. A cell supernatant was obtained 24 hours after stimulation, and the amount of MCP-1 production was measured by using a human MCP-1 eraser kit (R&D Corp.). The amount of production was calculated based on a calibration curve formed in the range of 31.2 to 2000 pg/ml by using MCP-1 standards contained in the kit. The results indicate that BPS inhibits dose-dependently the production of MCP-1 of the THP-1 cells induced by 10 μg/ml of LPS (FIG. 1).

Example 2

Action on Expression of MCP-1 mRNA of Human Monocyte/Macrophage System Cells THP-1

Figure 2:
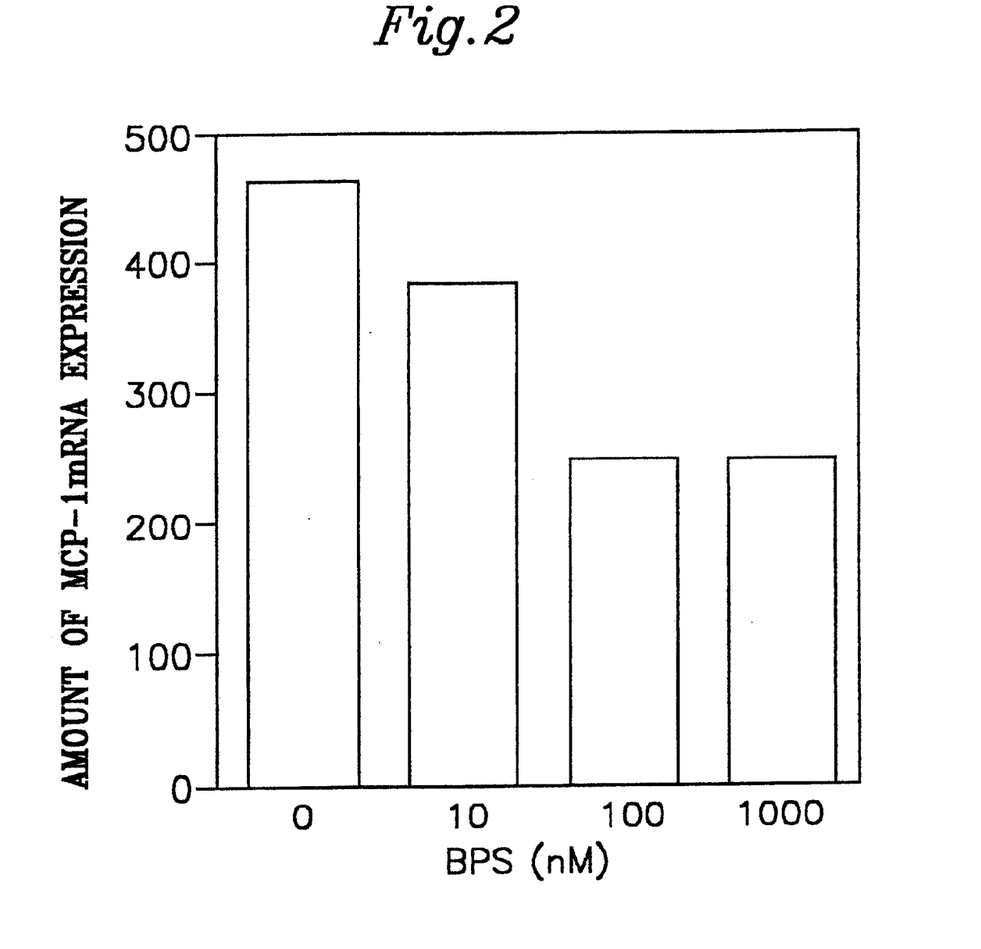
FIG. 2 shows the BPS action on the amount of MCP-1 mRNA expression of THP-1 cells stimulated with LPS.

The action of BPS on MCP-1 production was examined by using human monocyte/macrophage system leukemic cells THP-1 and the amount of mRNA expression as an index. LPS reactive substrains were isolated from THP-1 cells, and cultured in a RPMI 1640 medium containing 10% FCS in a flask. THP-1 cells ($1 \times 10^6$ cells) were dispensed to a petri dish having a diameter of 10 cm, and activated with 10 μg/ml of LPS. BPS was added 5 minutes before LPS stimulation. The total of RNA was extracted with a LiCl-urea solution (6M urea/3M LiCl/5 mM EDTA) 24 hours after stimulation, and dissolved in a TE solution (10 mm Tris-HCl/lmM EDTA, pH 8.0), and then proteins were removed with phenol and chloroform, followed by RNA recovery by ethanol precipitation. RNA was developed by formaldehyde-modified 1% agarose gel, and transferred to a Hybond-N filter (Amersham Corp.), and then MCP-1 mRNA was detected by using a $^{32}$ human MCP-1 probe. The detection was carried out by using a X-ray film or imaging film, and the amount of expression was digitized by BAS2000. The results indicate that BPS inhibits dose-dependently expression of MCP-1 mRNA of THP-1 cells stimulated by LPS (FIG. 2)

Example 3

Action on MCP-1 Production of Human Peripheral Blood-derived Monocytes

Figure 3:
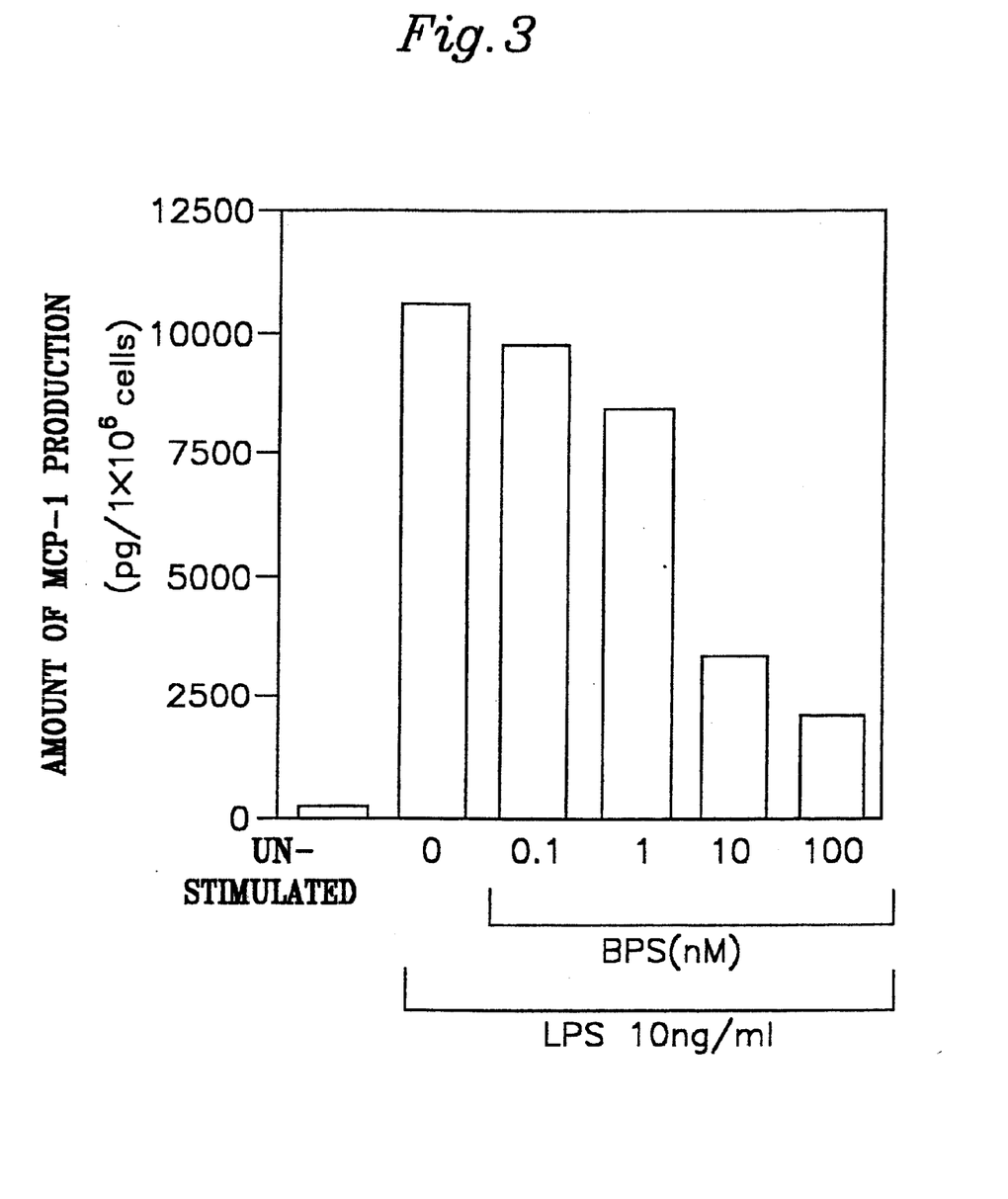
FIG. 3 shows the BPS action on MCP-1 production of human peripheral blood monocytes stimulated with LPS.

The action of BPS on MCP-1 production was studied by using human peripheral blood-derived monocytes. The heparinized peripheral blood of a healthy person was superposed on a histo-pack (Sigma Corp.), and centrifuged to obtain a monocyte layer. The thus-obtained monocyte layer was reacted with magnetic beads (Miltenyi Biotec Corp.) of anti—CD3 and anti—CD19, and monocytes were purified by a negative selection method using a MACS column (Miltenyi Biotec Corp.). The thus-obtained monocytes were re-suspended in a RPMI 1640 medium so that $1 \times 10^6$ cells/ml of cells were obtained. The cells were dispensed to a 48-well plate, and activated with 10 ng/ml of LPS. BPS was added 5 minutes before LPS stimulation. A cell supernatant was obtained 24 hours after stimulation, and the amount of MCP-1 produced was measured by using a human MCP-1 eraser kit. The amount of production was calculated based on a calibration curve formed in the range of 31.2 to 2000 pg/ml by using MCP-1 standards contained in the kit. The results indicate that BPS inhibits dose-dependently the production of MCP-1 of human peripheral blood monocytes induced by 10 ng/ml of LPS (FIG. 3)

Example 4

Action on Production of MCP-3 of Human Monocyte/Macrophage System Cells THP-1

Figure 4:
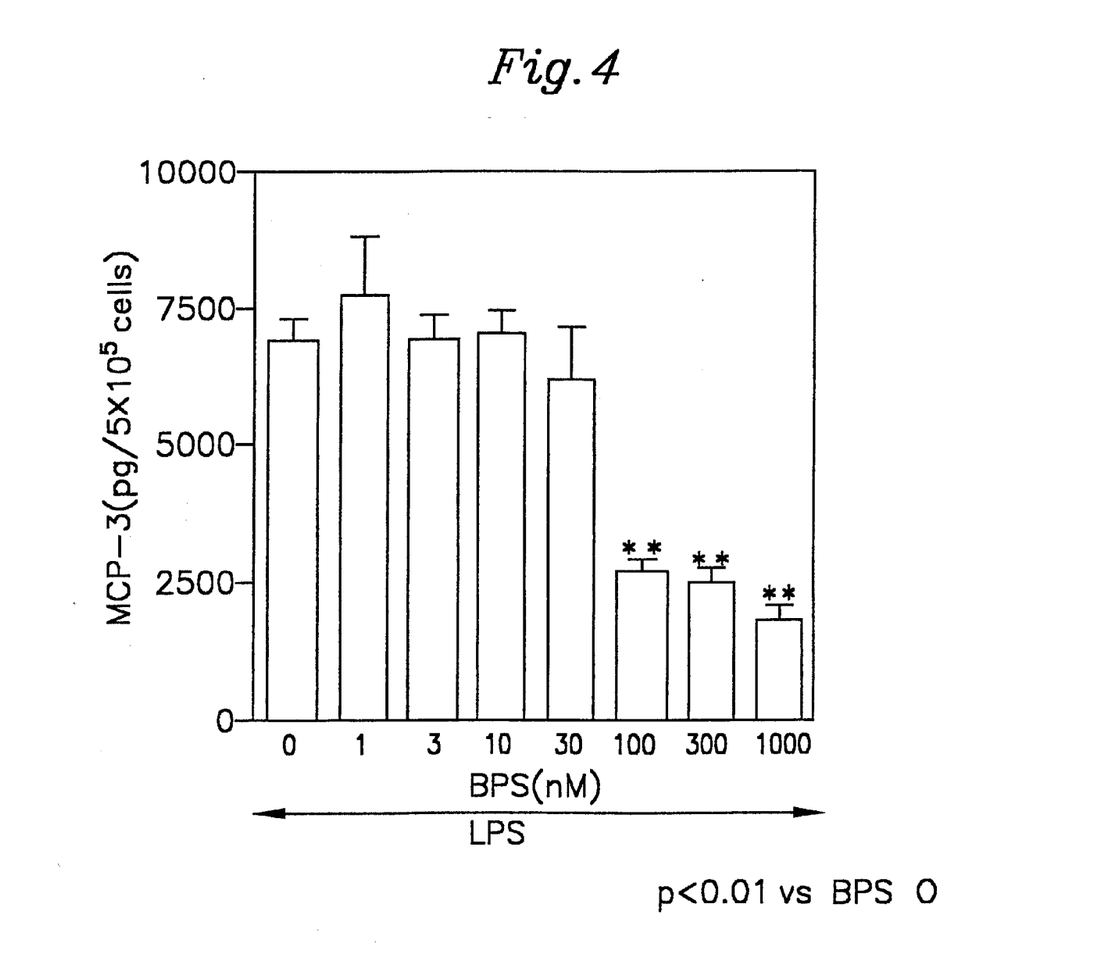
FIG. 4 shows the BPS action on MCP-3 production of THP-1 cells stimulated with LPS.

The action of BPS on MCP-3 production was examined by using human monocyte/macrophage system leukemic cells THP-1. LPS reactive substrains were isolated from THP-1 cells, and cultured in a RPMI 1640 medium containing 10% FCS in a flask. THP-1 cells ($1 \times 10^6$ cells) were dispensed to a 12-well plate, and activated with 10 μg/ml of LPS. BPS was added 5 minutes before LPS stimulation. A cell supernatant was obtained 24 hours after stimulation, and the amount of the MCP-3 produced was measured by using a MCP-3 detection method developed by the inventors. The amount of production was calculated based on a calibration curve formed in the range of 0.195 to 12.5 ng/ml by using MCP-3 standards. The results indicate that BPS inhibits dose-dependently not only MCP-1 production of THP-1 cells (FIG. 1) but also the production of MCP-3 of THP-1 cells induced by 10 μg/ml of LPS (FIG. 4)

Example 5

Figure 5:
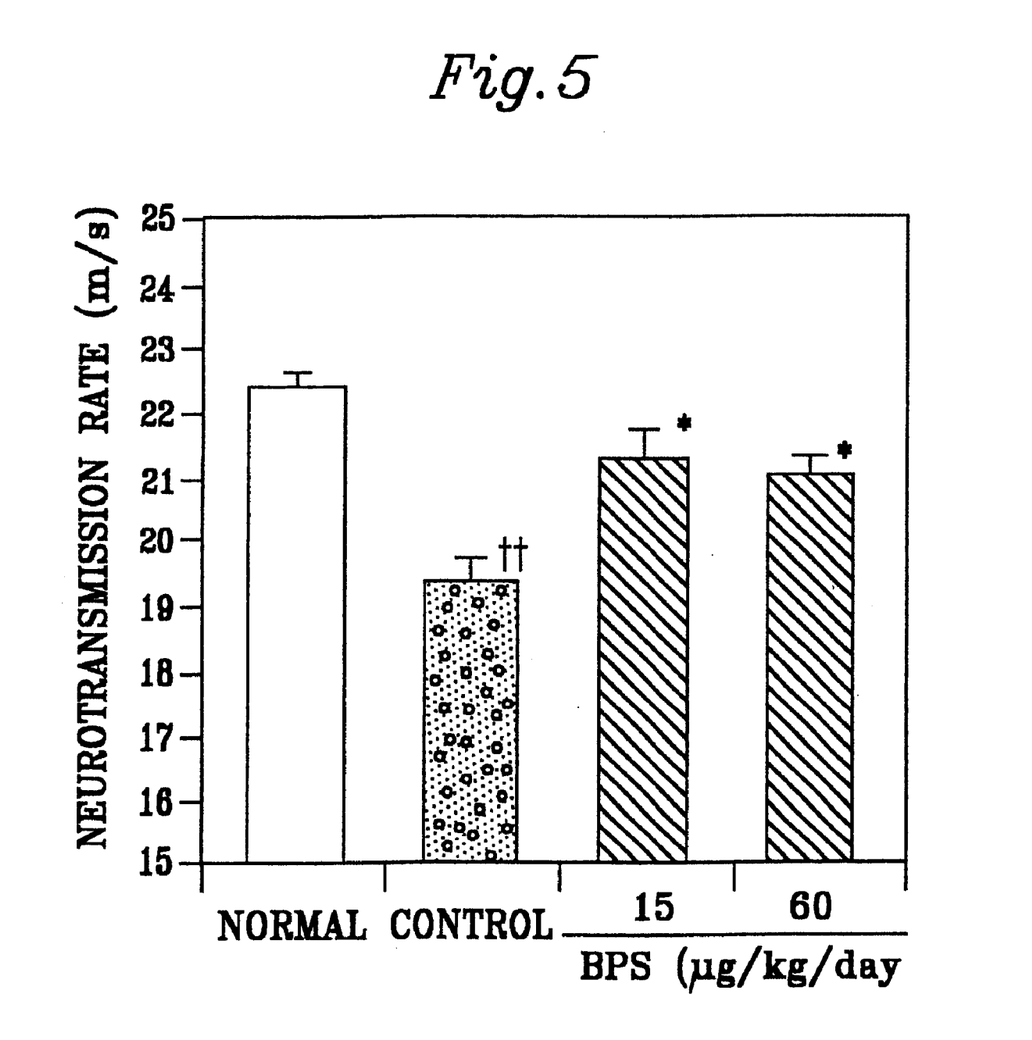
FIG. 5 shows the effect of BPS administration on the neurotransmission rate of streptozotocin-induced diabetic rats.

Effect of BPS Administration on MCP-1 Amount in LPS-induced Blood of Diabetic Rats SD male rats were intravenously administered with 45 mg/kg streptozotocin to induce diabetes. At the eighth week after 2 mg/kg of LPS was administered to the rats to measure the MCP-1 amount in the blood before administration and 3 and 6 hours after administration. BPS was orally administered to the rats 30 minutes before LPS administration. Rats of the same age as the diabetic rat group were used as a normal group. The results are shown in Table 1. In the diabetic rats, MCP-1 production was significantly increased by administering LPS, as compared with the normal rats. In the rat group administered with BPS, MCP-1 production was significantly inhibited, thereby indicating an in vivo experiment that abnormal production of MCP-1 due to diabetes is improved by BPS. As a result of measurement of the neurotransmission rate of the ischiatic nerve by using the same diabetic rats, a decrease in the neurotransmission rate due to diabetes was significantly improved by BPS (FIG. 5)

TABLE 1

Effect of Oral Administration of BPS on MCP-1 amount in LPS-Induced Blood of Rats Administered with Streptozotocin

| | | MCP-1 amount in blood (ng/ml) | | |
| --- | --- | --- | --- | --- |
| Treatment | n | Before LPS administration | 3 hours after | 6 hours after |
| Normal group | 4 | 0.30 ± 0.11 | 7.39 ± 1.22‡‡ | 3.86 ± 1.44‡ |
| Diabetic group | | | | |
| Untreated | 4 | 0.30 ± 0.04 | 13.47 ± 4.40# | 9.42 ± 1.59 |
| BPS administered | 3 | 0.39 ± 0.13 | 7.27 ± 2.55‡‡ | 4.82 ± 4.40‡ |

Numerals represent average ± standard deviation
‡p <0.05, ‡‡: p < 0.01 in comparison with the untreated diabetic group (Student's test)
The value obtained from 3 samples because of defects in a sample.

Example 6

Action on MCP-1 Production of Human Monocyte/Macrophage System Cells THP-1

Figure 6:
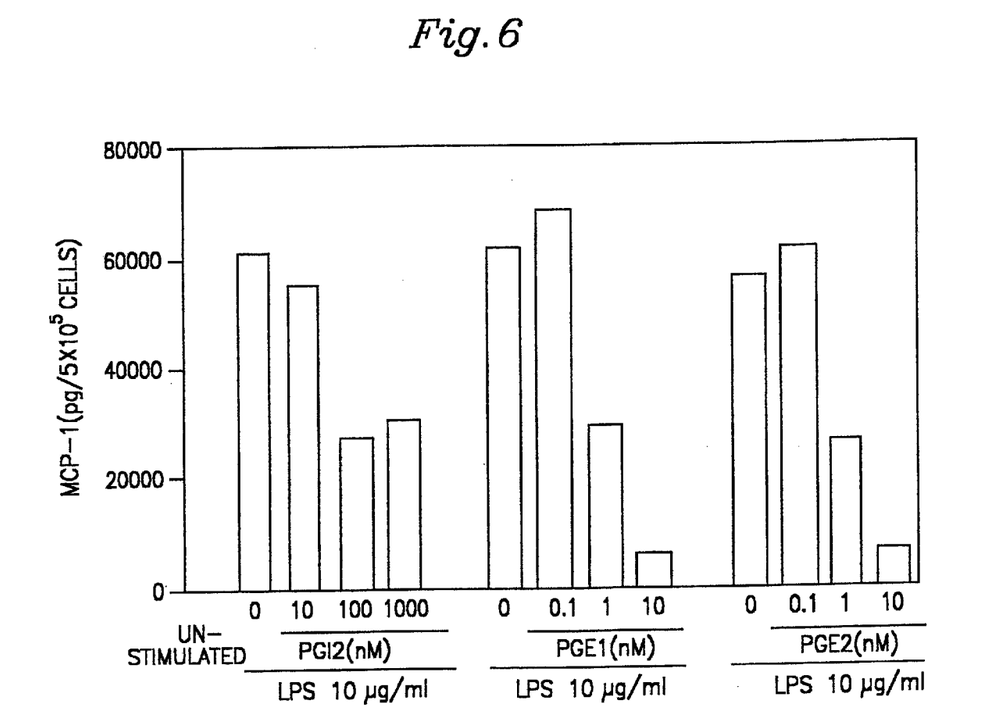
FIG. 6 shows the actions of various PG compounds on MCP-1 production of THP-1 cells stimulated with LPS.

The actions of prostaglandin $I_2$ ($PGI_2$), prostaglandin $E_1$ ($PGE_1$), and prostaglandin $E_2$ ($PGE_2$) on MCP-1 production were examined by the same method as Example 1. As a result, MCP-1 production was inhibited by $PGI_2$, $PGE_1$, and $PGE_2$ (FIG. 6).

Example 7

Action on MCP-1 Production of Human Monocyte/Macrophage System Cells THP-1

The actions of the compounds shown in the table below on MCP-1 production by the same method as Example 1.

The action of each of the compounds was shown by an inhibition rate. As a result, MCP-1 production was inhibited by these compounds (Table 2).

Example 8

Action on MCP-1 Production of Monocytes Derived from Human Peripheral Blood

Monocytes derived from the human peripheral blood were isolated by the same method as Example 3, and stimulated with 25 nM 12-o-tetradecanoylphorbol 13-acetate (TPA) to induce MCP-1 production. The action of BPS on MCP-1 production was studied. As a result, 224.7 pg/1×10$^6$ cells of MCP-1 produced by TPA stimulation was decreased to 184 pg/1×10$^6$ cells by 100 nM BPS, and thus it was confirmed that MCP-1 production due to TPA stimulation is inhibited by BPS.

Example 9

Action on MCP-1 Production of Monocytes Derived from Human Peripheral Blood

The action of prostaglandin $J_2$ ($PGJ_2$) on MCP-1 production due to LPS or TPA simulation was studied by the same method as Examples 3 and 8 using monocytes derived from the human peripheral blood. $PGJ_2$ was added 1 minute before stimulation. As a result, MCP-1 production due to stimulation by either LPS or TPA was inhibited by $PGJ_2$ (Table 3).

TABLE 2

Inhibition rates of various PG derivatives to MDP-1 production of THP-1 cells

| Structural formula | Inhibition rate (%) | Structural formula | Inhibition rate (%) |
|---|---|---|---|
| [structure with COOH, benzofuran, phenyl] | 58 | [structure with OH, benzofuran, phenoxy] | 4 |
| [structure with COOH, benzofuran, cyclohexyl] | 85 | [structure with OH, dimethyl, benzofuran, phenoxy] | 28 |
| [structure with O-COOH, benzofuran, phenyl] | 61 | [structure with COOH, benzofuran, cyclohexyl] | 87 |

TABLE 3

Action of $PGJ_2$ on MCP-1 production of human peripheral blood monocytes

| Treatment | MCP-1 (pg/$10^6$ cells) |
|---|---|
| LPS 10 ng/ml | 21872 |
| LPS 10 ng/ml + $PGJ_2$ 10 μM | 6 |
| TPA 25 nM | 225 |
| TPA 25 nM + $PGJ_2$ 10 μM | 2 |

Example 10

Action on RANTES Production of Human Monocyte/Macrophage System Cells THP-1

THP-1 cells were prepared by the same method as Example 1, and stimulated with LPS to induce RANTES production. The amount of RANTES production was measured by RANTES eraser kit (R&D Corp.). The action of $PGJ_2$ on RANTES production was studied. As a result, 5177 pg/5×$10^5$ cells of RANTES produced by LPS stimulation was decreased to 2403 pg/5×$10^5$ cells by 10 μM $PGJ_2$, and it was thus confirmed that RANTES production due to LPS stimulation is inhibited by $PGJ_2$.

Example 11

Figure 7A:
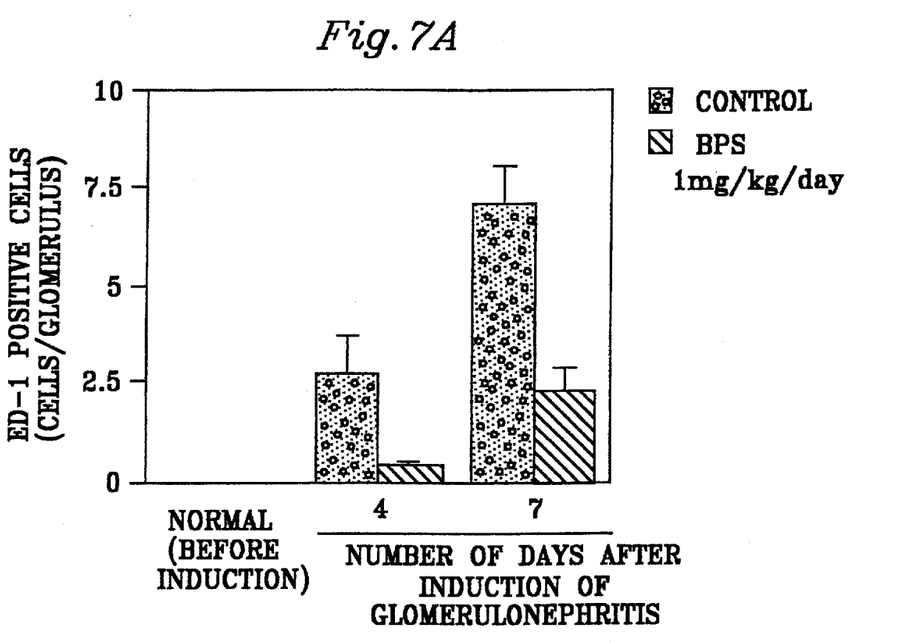
Figure 7B:
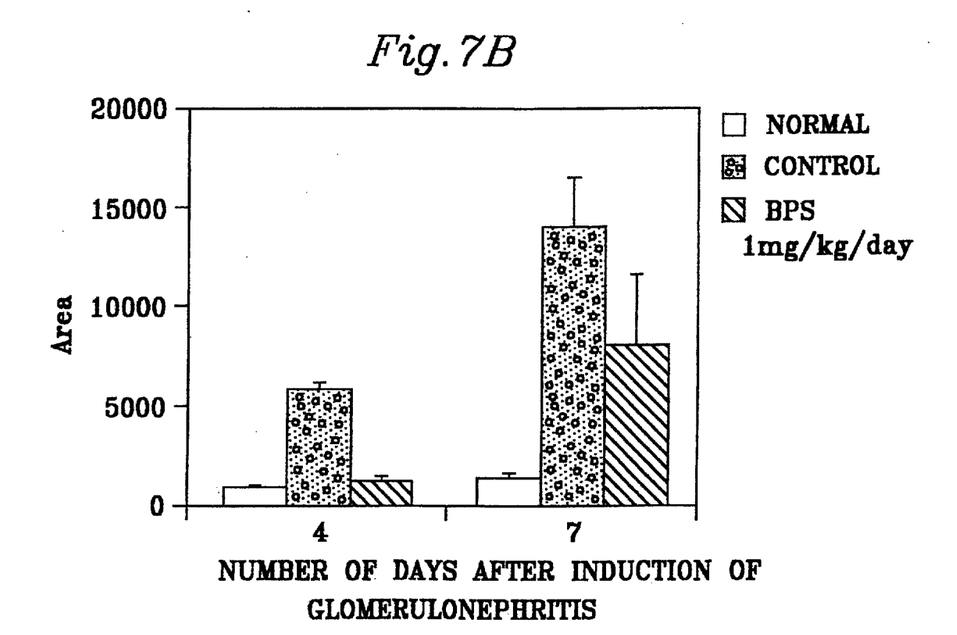
Figure 8:
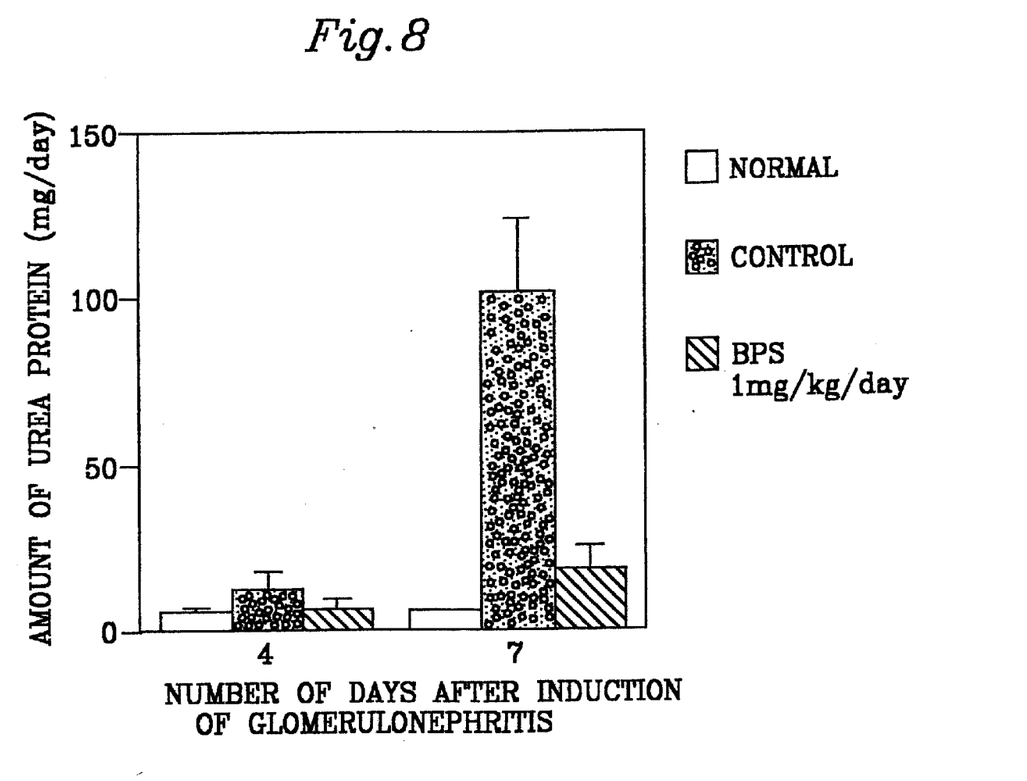
FIG. 8 shows the effect of BPS administration on the amount of urea protein in a glomerulonephritis model

Action on MCP-1 production and macrophage infiltration in kidney in glomerulonephritis rat model:

A glomerular basement membrane was administered with an antibody to form a glomerulonephritis rat model. The rats used were 9-week old male WKY rats which were purchased from Japan Charles River. The antibody was obtained by immunizing the rat glomerular basement membrane against rabbits. The amount of proteins in urea was increased 4 days after administration of the antibody, reached a plateau 11 days after administration, and then did not change up to the death of the rats. A glomerular lesion such as formation of the crescent was also confirmed by pathological findings, and an irreversible glomerulonephritis model could be formed by administering the antibody to the anti-glomerular basement membrane. MCP-1 production in the kidney was increased with the passage of days after administration of the antibody to produce infiltration of leukocytes such as macrophages and the like. 1 mg/kg of BPS was orally administered on consecutive days to study the action of BPS on MCP-1 production and infiltration of the macrophages. The MCP-1 production was studied by purifying messenger RNA (mRNA) from the rat kidneys, and determining the amount of MCP-1 mRNA expression by quantitative PCR. The macrophage infiltration was studied by immunostaining with an anti-macrophage antibody (ED-1), and then counting the macrophages infiltrated into the glomeruli under a microscope. As a result of comparison between a group administered with distilled water and a group administered with BPS 4 days and 7 days after administration of the antibody, in the group administered with BPS, infiltration of macrophage per glomerulus was significantly inhibited in parallel with inhibition of MCP-1 mRNA expression (FIGS. 7a and b). Using the same glomerulonephritis model, the action of BPS on the amount of urea protein was studied 4 days and 7 days after administration of the antibody. As a result, the amount of protein was significantly decreased by BPS both 4 days and 7 days after the administration (FIG. 8).

INDUSTRIAL APPLICABILITY

Prostaglandin derivatives have the action to inhibit C—C chemokine production, and are effective to cure circulatory diseases, inflammation, allergic diseases, renal diseases, etc.

What is claimed is:

1. A method of inhibiting mammalian C—C chemokine synthesis comprising delivering an effective amount of a prostaglandin $I_2$ derivative to a C—C chemokine synthesis pathway, wherein the prostaglandin $I_2$ derivative is a 4,8-inter-m-phenylene prostaglandin $I_2$ derivative represented by the following formula, or a pharmacologically acceptable salt thereof:

wherein $R^1$ represents the following:
(A) $COOR^2$ wherein $R^2$ is:
1) hydrogen or a pharmacologically acceptable cation;
2) straight chain alkyl having 1 to 12 carbon atoms, or branched alkyl having 3 to 14 carbon atoms;
3) —Z—$R^3$
  wherein Z is a valence bond or straight chain or branched alkylene represented by $C_tH_{2t}$, wherein t represents an integer of 1 to 6, and $P^3$ represents cycloalkyl having 3 to 12 carbon atoms or substituted cycloalkyl having 3 to 12 carbon atoms and 1 to 3 substituents $R^4$ each of which is hydrogen or alkyl having 1 to 5 carbon atoms;
4) —$(CH_2CH_2O)_nCH_3$
  wherein n is an integer of 1 to 5;
5) —Z—$Ar^1$
  wherein Z is defined above, and $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein a substituent is at least one of chlorine, fluorine, iodine, trifluoromethyl, alkyl having 1 to 4 carbon atoms, nitro, cyano, methoxy, phenyl, phenoxy, p-acetoamidobenzamide, —CH=N—NH—C(=O)—$NH_2$), —NH—C(=O)Ph, —NH—C(=O)—$CH_3$ and —NH—C(=O)—$NH_2$);
6) —$C_tH_{2t}COOR^4$
  wherein $C_tH_{2t}$ and $R^4$ are defined above;
7) —$C_tH_{2t}N(R^4)_2$ wherein —CtH2t and $R^4$ are defined above;
8) —CH($R^5$)—C(=O)—$R^6$
  wherein $R^5$ is hydrogen or benzoyl, and $R^6$ is phenyl, p-bromophenyl, p-chlorophenyl, p-biphenyl, p-nitrophenyl, p-benzamidophenyl, or 2-naphthyl;
9) —$C_pH_{2p}$—W—$R^7$
  wherein W is —CH=CH—, —CH=$CR^7$ or —C≡C—, and $R^7$ is hydrogen or straight chain or branched alkyl or aralkyl having 1 to 30 carbon atoms, and p is an integer of 1 to 5; or
10) —CH($CH_2OR^8)_2$
  wherein $R^8$ is alkyl or acyl having 1 to 30 carbon atoms;

(B) —CH$_2$OH;
(C) —C(=O)N(R$^9$)$_2$
wherein R$^9$ is hydrogen, straight chain alkyl having 1 to 12 carbon atoms, branched alkyl having 3 to 12 carbon atoms, cycloalkyl having 3 to 12 carbon atoms, cycloalkylalkylene having 4 to 13 carbon atoms, phenyl, substituted phenyl (wherein the substituent is defined in (A) (5)), aralkyl having 7 to 12 carbon atoms, or —SO$_2$R$^{10}$ wherein R$^{10}$ is alkyl having 1 to 10 carbon atoms, cycloalkyl having 3 to 12 carbon atoms, phenyl, substituted phenyl (the substituent is defined in (A) (5)), or aralkyl having 7 to 12 carbon atoms, two R$^9$ groups may be the same or different, and when one of the R$^9$ groups is —SO$_2$R$^{10}$, the other R$^9$ is not —SO$_2$R$^{10}$; or
(D) —CH$_2$OTHP (THP is a tetrahydropyranyl group);
A is the following:
1) —(CH$_2$)$_m$—;
2) —CH=CH—CH$_2$—;
3) —CH$_2$—CH=CH—;
4) —CH2—O—CH$_2$—;
5) —CH=CH—;
6) —O—CH$_2$—; or
7) —(≡C—;
wherein m represents an integer of 1 to 3;
D is hydrogen, alkyl having 1 to 4 carbon atoms, chlorine, bromine, fluorine, formyl, methoxy or nitro;
G is —X—C(R$^{11}$)(R$^{12}$)OR$^{13}$
wherein R$^{11}$ is hydrogen, alkyl having 1 to 4 carbon atoms; R$^{13}$ is hydrogen, acyl having 1 to 14 carbon atoms, aroyl having 6 to 15 carbon atoms, tetrahydropyranyl, tetrahydrofuranyl, 1-ethoxythienyl, or t-butyl; X is the following;
1) —CH$_2$—CH$_2$—;
2) —CH=CH—; or
3) —C≡C—; and
R$^{12}$ is the following;
1) straight chain alkyl having 1 to 12 carbon atoms, or branched alkyl having 3 to 14 carbon atoms;
2) —Z—Ar$^2$
wherein Z is defined above, and Ar$^2$ represents phenyl, α-naphthyl, β-naphthyl, or phenyl substituted by at least one chlorine, bromine, fluorine, iodine, trifluoromethyl, alkyl having 1 to 4 carbon atoms, nitro, cyano, methoxy, phenyl or phenoxy;
3) —C$_t$H$_{2t}$OR$^{14}$
wherein C$_t$C$_{2t}$ is defined above, and R$^{14}$ represents straight chain alkyl having 1 to 6 carbon atoms, branched alkyl having 3 to 6 carbon atoms, phenyl, phenyl substituted by at least one chlorine, bromine, fluorine, iodine, trifluoromethyl, alkyl having 1 to 4 carbon atoms, nitro, cyano, phenyl or phenoxy, cyclopentyl, cyclohexyl, or cyclopentyl or cyclohexyl substituted by 1 to 4 straight chain alkyl groups having 1 to 4 carbon atoms;
4) —Z—R$^3$
wherein Z and R$^3$ are defined above;
5) —C$_t$H$_{2t}$—CH=C(R$^{15}$)R$^{16}$
wherein C$_t$H$_{2t}$ is defined above, and R$^{15}$ and R$^{16}$ each represent hydrogen, methyl, ethyl, propyl, or butyl; or
6) —C$_u$H$_{2u}$—C≡C—R$^{17}$
wherein u is an integer of 1 to 7, C$_u$H$_{2u}$ represents straight chain or branched alkyl, and R$^{17}$ represents straight chain alkyl having 1 to 6 carbon atoms;
E is hydrogen or —OR$^{18}$
wherein R$^{18}$ represents acyl having 1 to 12 carbon atoms, aroyl having 7 to 15 carbon atoms, or R$^2$ (wherein R$^2$ is defined above); and the formula represents a d, l or dl form.

2. A method according to claim 1, wherein inhibiting mammalian C—C chemokine synthesis is performed in mammals having diseases characterized by abnormal accumulation or activation of leukocytes.

3. A method according to claim 2, wherein said leukocytes showing abnormal accumulation or activation are monocytes or macrophages.

4. A method according to claim 3, wherein said leukocytes showing abnormal accumulation or activation comprise at least one type of eosinophils, basophils, and lymphocytes.

5. A method according to claim 1, inhibiting mammalian C—C chemokine synthesis is performed in mammals having diseases selected from the group consisting of chronic intractable inflammation, pneumonocirrhosis, pneumonia, ARDS, ulcerative colitis, chronic rheumatoid arthritis, atopic dermatitis, Crohn's disease, parasitic diseases, and endometriosis.

6. A method according to claim 1, wherein the 4,8-inter-m-phenylene prostaglandin I$_2$ derivative is beraprost or a salt thereof.

7. A method according to claim 1, wherein said C—C chemokine is MCP-1, MCP-3, or RANTES.

8. A method according to claim 1, wherein inhibiting mammalia C—C chemokine synthesis is performed in mammals having diseases associated with increased levels of C—C chemokines.

9. A method of treating diseases selected from the group consisting of chronic intractable inflammation, pneumonocirrhosis, pneumonia, ARDS, ulcerative, colitis, chronic rheumatoid arthritis, atopic dermatitis, Crohn's disease, parasitic diseases, and endometriosis, which comprises administering an effective amount of a 4,8-inter-m-phenylene prostaglandin I$_2$ derivative represented by the formula shown in claim 1 or a pharmacologically acceptable salt thereof.

* * * * *

UNITED STATES PATENT AND TRADEMARK OFFICE
CERTIFICATE OF CORRECTION

PATENT NO.    : 6,653,345 B2
DATED         : November 25, 2003
INVENTOR(S)   : Kurumatani et al.

It is certified that error appears in the above-identified patent and that said Letters Patent is hereby corrected as shown below:

Column 4,
Line 24, please delete "N" before "and"; and
Line 30, please change "CH=CR" to -- $CH=CH^7$ --.

Column 5,
Line 43, please insert the following paragraphs:
-- Although preferred examples of prostaglandin I derivatives of the present invention include beraprost or salts thereof represented by the following formula (II), ataprost, iroporst, clinprost, ciprostene, naxaprostene, taprostene, cicaprost, pimilprost, CH-169, CS570, and the like, the prostaglandin I derivatives are not limited to these derivatives.

The prostanoic acid derivatives of the present invention can be produced by known methods. For example, compounds represented by formula (I) or salts thereof can be produced by the method disclosed in Japanese Examined Patent Publication No. 1-53672. --

Column 7,
Line 27, please change "$^{32}$human" to -- $^{32}$p-labeled human --.

Column 12,
Line 30, please change "$P^3$" to -- $R^3$ --.

Column 13,
Line 25, please change "-(=C-" to -- -C=C- --.

UNITED STATES PATENT AND TRADEMARK OFFICE
CERTIFICATE OF CORRECTION

PATENT NO. : 6,653,345 B2
DATED : November 25, 2003
INVENTOR(S) : Kurumatani et al.

It is certified that error appears in the above-identified patent and that said Letters Patent is hereby corrected as shown below:

Column 14,
Line 30, please insert -- wherein -- after "claim 1,"

Signed and Sealed this

Sixth Day of April, 2004

JON W. DUDAS
*Acting Director of the United States Patent and Trademark Office*